United States Patent [19]

Ahmad et al.

[11] Patent Number: 5,112,611
[45] Date of Patent: May 12, 1992

[54] PHARMACEUTICAL COMPOSITIONS FOR AIDING HUMAN DIGESTION

[75] Inventors: Mohammad R. Ahmad, Glenview; Oscar A. Barke, Skokie, both of Ill.

[73] Assignee: Floss Products Corporation, Morton Grove, Ill.

[21] Appl. No.: 579,824

[22] Filed: Sep. 10, 1990

[51] Int. Cl.⁵ .................. A61K 35/78; A61K 37/54
[52] U.S. Cl. .............................. 424/195.1; 424/94.65
[58] Field of Search .......................... 424/195.1, 94.65

[56] References Cited

U.S. PATENT DOCUMENTS

| 115,698 | 6/1871 | Burroughs | 424/195.1 |
| 3,493,652 | 2/1970 | Hartman | 424/94.65 |
| 4,447,412 | 5/1984 | Bilton | 424/16 |
| 4,477,434 | 10/1984 | Kosaka | 424/94 |

OTHER PUBLICATIONS

Steinmetz, E. F., Codex Vegetabilis 1957 Amsterdam #246, 577.
Perlmann, G. O., Proteolytic Enzymes, vol. XIX Methods in Enzymology Academic Press NY pp. 234-235.
Mahler, H. R., Biological Chemistry 2nd ed Harper & Row NY 1971 pp. 771-772.
Lewis, W. H. Medical Botany John Wiley & Sons NY 1977 pp. 224.
Reynolds, J. E. F. Martindale 28th Ed 1982 The Pharmaceutical Press, London, 4600-n p. 670.
Dore, James A., CRC Handbook of Medicinal Herbs CRC Press Boca Raton, Fla. 1985 pp. 100-101.
Barnhart, E. R., Physicians' Desk Reference 10th Ed. 1989 Medical Economics, N.J. p. 638.
The Merck Index 1989 11th Ed. Merck & Co. Rahway, N.J. #6965.

Primary Examiner—Johnnie R. Brown
Assistant Examiner—Ralph Gitomer
Attorney, Agent, or Firm—Charles F. Lind

[57] ABSTRACT

The disclosed pharmaceutical composition for aiding human digestion uses only the active ingredients of papain, hyssop and grapefruit extracts blended together, in preferred embodiments, with a gum base. In one embodiment, the active ingredients of papain and hyssop are in a ratio between 1:1 and 5:1 parts papain to parts hyssop; and the papain and grapefruit extracts are in a ratio between 1:1 and 10:1 parts papain to parts grapefruit extracts. The active ingredients can be between 3-8% of the overall mass of the digestive aid. A dosage concentration per piece of the digestive aid gum can be between 0.02-0.2 grams of papain, and the corresponding concentrations of the other active ingredients. The papain serves to stimulate digestion, the hyssop serves to soothe and clean one's mouth and throat, and the grapefruit serves to stimulate the generation of natural saliva in the mouth.

8 Claims, No Drawings

PHARMACEUTICAL COMPOSITIONS FOR AIDING HUMAN DIGESTION

BACKGROUND OF THE INVENTION

Food consumed by humans consists mainly of complex materials comprised of proteins, carbohydrates and fats. With the exception of a few foods, the materials cannot be absorbed into the body without first being transformed into simpler compounds. The human digestive system is in the form of a tubular alimentary tract; and although some digestion takes place near the intake end thereof, between the mouth and the stomach, most of the digestion takes place and is completed in the small intestine downstream of the stomach and more toward the discharge end of the tract.

In the digestion process, the foods are mechanically broken down by chewing and/or other muscular action including by peristalsis in the stomach and intestines, and are mixed with secretions containing enzymes, to invoke the resulting chemical changes needed for body absorption. The body normally produces the needed enzymes naturally; but delays or inadequate productions thereof can provide for slow or incomplete digestion, to the extent even of creating varying degrees of discomfort caused frequently by the generation of gas.

Artificially produced or man-made indigestive products are known and available, to be independently taken as needed or desired, effective to neutralize gas buildup or the like in the digestive tract. However, such products generally are intended to be taken after eating and after experiencing some discomfort. Also, the nature of and/or strength of some ingredients in such products might be destructive and/or excessive to allow regular continued use of them.

SUMMARY OF THE INVENTION

A basic object of this invention is to provide a human digestive aid comprised of natural organic materials, that can be independently taken as needed or desired, before or after eating, and in fact preferably before one may experience any digestive discomfort and on a regular basis.

A preferred mode of the digestive aid will be in the form of a chewing gum, which when chewed, will release its beneficial ingredients to combine with one's natural saliva and be swallowed to enter the digestive track over an extended period and in gradual dosages.

One feature of this invention provides a human digestive aid comprised of the combination of the active ingredients of papain and hyssop, blended together in possible ratios between 1:1 and 5:1 parts papain to parts hyssop.

Another feature of this invention provides a human digestive aid comprised of generally the same combinations of the active ingredients of papain and hyssop, and further having grapefruit extracts blended therewith, in possible ratios between 1:1 and 10:1 parts papain to parts grapefruit.

More detailed features of this invention may provide for a dosage concentration of between 0.02-0.2 grams of papain, and the corresponding dosages of the other ingredients, per piece of such digestive aid or gum.

DETAILED DESCRIPTION OF PREFERRED EMBODIMENTS OF THE INVENTION

The preferred embodiments of the human digestive aid to be disclosed herein are comprised of natural organic materials including papain and hyssop, or papain, hyssop and grapefruit. Papain is an enzyme that can be obtained from the pulverized body of papaya fruit, including its pulp, skin and seeds; and is commercially available in dry granular form or in liquid extract form. Hyssop and grapefruit each can be obtained as a liquid extract, of the herb and of the fruit pulp and juices respectively.

EXAMPLE 1

Papain and hyssop may be blended together in a preferred ratio of two parts papain for one part hyssop, or 2:1 parts papain to parts hyssop. However, it is possible to vary this ratio somewhat, such as in possible ratios between 1:1 and 5:1 parts papain to parts hyssop.

A sweetener such as sorbitol and/or a flavor additive such as mint may be added to the digestive aid end product, as needed for taste.

A preferred form of the digestive aid would be as a gum, as the need to chew the gum generates natural saliva in the mouth, which then serves to extract and/or blend with the active ingredients thereof. The resultant liquid would eventually be swallowed, to reach the stomach and lower portions of the digestive tract.

A commercially available gum base would be used and may constitute between 50-95% of the overall mass of the digestive aid end product while the blended active papain and hyssop ingredients may comprise approximately 3-8% of the overall mass of the end product. The sweetener, flavor enhancer or other additives can constitute the balance of the digestive aid product.

Papain serves to stimulate the digestion, while the hyssop serves to soothe and clean one's mouth and throat.

EXAMPLE 2

A second preferred embodiment of the human digestive aid is comprised of natural organic active ingredients of the papain and hyssop, and the active ingredient of grapefruit extracts blended therewith. The papain and hyssop may be blended together in the same ratio of EXAMPLE 1, and the grapefruit extracts may be blended therewith in a ratio of two parts papain for every part of grapefruit, or 2:1 parts papain to parts grapefruit. Alternatively, the grapefruit extracts can be blended therewith, in possible ratios between 1:1 and 10:1 parts papain to parts grapefruit.

A sweetener such as sorbitol and/or a flavor additive such as mint may be added to the digestive aid product, as needed for taste; which could vary from EXAMPLE 1 as the grapefruit extracts varies the taste somewhat toward the sour.

Again, a preferred form of this combination would be as a gum, where the gum base may constitute between 50-95% of the overall mass of the digestive aid end product. The blended active papain, hyssop and grapefruit ingredients may comprise approximately 3-8% and the sweetener or other additives can constitute the balance of the digestive aid product.

The papain serves to stimulate digestion, the hyssop serves to soothe and clean one's mouth and throat, and the grapefruit serves to stimulate the generation of natural saliva in the mouth.

In both examples, a dosage concentration of between 0.02-0.2 grams of papain, and the corresponding concentrations of the other ingredients, would be preferred per piece of such digestive aid gum.

Other additives may be added to the digestive aid product, including possibly different vitamin supplements such as vitamins C, A and/or D, or phosphorus and/or calcium. These components have not been included in the examples given, as they would not change the inventive aspect of the claimed invention.

Also, the active ingredients as held in the gum base provide a delayed release over an extended period of time of several minutes at least, for more gradual dosage releases and concentrations and for more effective utilization of the digestive aid.

While specific embodiments of the invention have been disclosed, the invention is to be limited only by the scope of the following claims.

What is claimed as our invention is:

1. A pharmaceutical composition for aiding human digestion essentially consisting of the combination of the active ingredients of papain, hyssop and grapefruit extracts blended together, the papain and hyssop being in a ratio between 1:1 and 5:1 parts papain to parts hyssop and the papain and grapefruit extracts being in a ratio between 1:1 and 10:1 parts papain to parts grapefruit, and a carrier blended with the active ingredients.

2. A pharmaceutical composition for aiding human digestion according to claim 1, further including the carrier being a gum base to provide the pharmaceutical composition is in the form of a gum to be administered by chewing, and said active ingredients consisting of between 3-8% of the overall mass of the composition.

3. A pharmaceutical composition for aiding human digestion according to claim 1, further including the papain and hyssop being blended together in a ratio of substantially 2:1 parts papain to parts hyssop.

4. A pharmaceutical composition for aiding human digestion according to claim 1, further including the papain and grapefruit extracts being blended together in a ratio of substantially 2:1 parts papain to parts grapefruit extracts.

5. A pharmaceutical composition for aiding human digestion according to claim 1, further including the papain and hyssop being blended together in a ratio of substantially 2:1 parts papain to parts hyssop, and the papain and grapefruit extracts being blended together in a ratio of substantially 2:1 parts papain to parts grapefruit extracts.

6. A pharmaceutical composition for aiding human digestion according to claim 5, further including the carrier being a gum base to provide the pharmaceutical composition is in the form of a gum to be administered by chewing, and said active ingredients consisting of between 3-8% of the overall mass of the composition.

7. A pharmaceutical composition for aiding human digestion according to claim 6, further wherein the per dosage of such composition being in the range of 0.2-0.2 grams of papain and the corresponding concentration of the other active ingredients.

8. A pharmaceutical composition for aiding human digestion according to claim 2, further wherein the per dosage of such composition being in the range of 0.02-0.2 grams of papain and the corresponding concentration of the other active ingredients.

* * * * *